United States Patent
Snyder

(10) Patent No.: US 8,980,576 B2
(45) Date of Patent: *Mar. 17, 2015

(54) PROCESS TO AVOID INHIBITION OF ACETOGENS BY CO

(71) Applicant: Ineos Bio SA, Lisle, IL (US)

(72) Inventor: David Scott Snyder, Fayetteville, AR (US)

(73) Assignee: Ineos Bio SA, Rolle (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/018,670

(22) Filed: Sep. 5, 2013

(65) Prior Publication Data

US 2014/0080117 A1    Mar. 20, 2014

Related U.S. Application Data

(60) Provisional application No. 61/702,824, filed on Sep. 19, 2012, provisional application No. 61/702,826, filed on Sep. 19, 2012, provisional application No. 61/702,832, filed on Sep. 19, 2012, provisional application No. 61/702,837, filed on Sep. 19, 2012.

(51) Int. Cl.
   *C12Q 1/02*     (2006.01)
   *B01D 57/00*    (2006.01)
   (Continued)

(52) U.S. Cl.
   CPC . *C12Q 3/00* (2013.01); *C12P 7/065* (2013.01); *C12P 7/08* (2013.01); *G01N 21/31* (2013.01); *G01N 33/84* (2013.01); *Y02E 50/17* (2013.01)
   USPC ............................................. 435/29; 95/11

(58) Field of Classification Search
   USPC .............................. 435/29; 95/11
   See application file for complete search history.

(56) References Cited

U.S. PATENT DOCUMENTS

| 5,173,429 A | 12/1992 | Gaddy |
| 5,807,722 A | 9/1998 | Gaddy |

(Continued)

FOREIGN PATENT DOCUMENTS

| WO | WO 2011/139163 | 11/2011 |
| WO | WO 2012/015317 | 2/2012 |

OTHER PUBLICATIONS

Solubility of Gases in Water, Engineering Tool Box, http://www.engineeringtoolbox.com/gases-solubility-water-d_1148.html, 2007, printed from https://web.archive.org/web/20071023034530/http://www.engineeringtoolbox.com/gases-solubility-water-d_1148.html on Oct. 24, 2014.*

(Continued)

*Primary Examiner* — Rosanne Kosson
(74) *Attorney, Agent, or Firm* — Ineos USA LLC

(57) ABSTRACT

A process is provided for fermenting CO-containing gaseous substrates. The process is effective for decreasing lag times and maintaining a culture in steady state by controlling CO concentration and minimizing effects of high or low CO concentrations during fermentation. The process includes providing syngas to a first fermentation zone, fermenting the syngas, and determining a CO concentration in a fermentation medium in the first fermentation zone. If the CO concentration in fermentation medium in the first fermentation zone has a value of about 0.12 μM or greater, then at least a portion of the syngas being provided to the first fermentation zone is provided to one or more subsequent fermentation zones in an amount effective for providing a CO concentration in any subsequent fermentation zone of about 0.12 μM or less.

32 Claims, 2 Drawing Sheets

(51) Int. Cl.
       *C12P 7/06*       (2006.01)
       *C12P 7/08*       (2006.01)
       *C12Q 3/00*       (2006.01)
       *G01N 21/31*      (2006.01)
       *G01N 33/84*      (2006.01)

(56) References Cited

U.S. PATENT DOCUMENTS

| | | |
|---|---|---|
| 6,136,577 A | 10/2000 | Gaddy |
| 6,774,148 B2 | 8/2004 | O'Rear |
| 7,285,402 B2 | 10/2007 | Gaddy |
| 2012/0003706 A1* | 1/2012 | Hickey ......................... 435/140 |

OTHER PUBLICATIONS

Hurst, Kendall et al., "Carbon monoxide partial pressure effects on the metabolic process of syngas fermentation" Biochemical Engineering Journal, Sep. 22, 2009, 48(2010) 159-165.

Kundu, Suman et al. "Direct Measurement of Equilibrium Constants for High-Affinity Hemoglobins" Biophysical Journal, Jun. 2003, vol. 84 3931-3940.

Riggs, Seth et al. "Measuring Carbon Monoxide Gas-Liquid Mass Transfer in a Stirred Tank Reactor for Syngas Fermentation" Biotechnol, 2006, 22, 903-906.

* cited by examiner

PROCESS TO AVOID INHIBITION OF ACETOGENS BY CO

This application claims the benefit of U.S. Provisional Application Nos. 61/702,824, 61/702,826, 61/702,832 and 61/702,837, all filed on Sep. 19, 2012, all of which are incorporated in their entirety herein by reference.

A process is provided for fermenting CO-containing gaseous substrates. More specifically, the process includes determining CO concentration in a first fermentation medium in a first fermentation zone. If the CO concentration in the first fermentation medium has a value of about 0.12 μM or greater, then at least a portion of the syngas provided to the first fermentation zone is provided to one or more subsequent fermentation zones in an amount effective for providing a CO concentration in any subsequent fermentation zone of about 0.12 μM or less.

BACKGROUND

Acetogenic microorganisms can produce ethanol from carbon monoxide (CO) through fermentation of gaseous substrates. Fermentations using anaerobic microorganisms from the genus *Clostridium* produce ethanol and other useful products. For example, U.S. Pat. No. 5,173,429 describes *Clostridium ljungdahlii* ATCC No. 49587, an anaerobic microorganism that produces ethanol and acetate from synthesis gas. U.S. Pat. No. 5,807,722 describes a method and apparatus for converting waste gases into organic acids and alcohols using *Clostridium ljungdahlii* ATCC No. 55380. U.S. Pat. No. 6,136,577 describes a method and apparatus for converting waste gases into ethanol using *Clostridium ljungdahlii* ATCC No. 55988 and 55989.

Many acetogenic microorganisms are poorly suited for industrial scale bioprocessing and have therefore not demonstrated commercial viability for this purpose. Such microorganisms have slow doubling time and low total productivities. In addition, many techniques for genetic manipulation (knockout, over-expression of transgenes via integration or episomic plasmid propagation) are inefficient, time-consuming, laborious, or non-existent.

Acetogenic microorganisms may be grown to produce ethanol from carbon monoxide. The growth process may involve culturing the acetogenic bacteria on increasing amounts of CO over time. Acetogenic microorganisms may be grown to produce ethanol from syngas that includes carbon monoxide. The growth process may involve culturing the acetogenic bacteria on increasing amounts of CO over time. High or low levels of CO in the fermentation may result in lower productivity

SUMMARY

A process is effective for maintaining high ethanol productivity levels during syngas fermentation. The process is effective for decreasing lag times and maintaining a culture in steady state by controlling CO concentration and minimizing effects of high or low CO concentrations during fermentation.

A syngas fermentation process includes providing syngas to a first fermentation zone, fermenting the syngas, and determining a CO concentration in a fermentation medium in the first fermentation zone. In accordance with the process, if the CO concentration in fermentation medium in the first fermentation zone has a value of about 0.12 μM or greater, then at least a portion of the syngas being provided to the first fermentation zone is provided to one or more subsequent fermentation zones in an amount effective for providing a CO concentration in any subsequent fermentation zone of about 0.12 μM or less.

In another aspect, a syngas fermentation process includes providing syngas to a first fermentor, fermenting the syngas, and determining a CO concentration in a fermentation medium in the first fermentor. In accordance with the process, if the CO concentration in fermentation medium in the first fermentor has a value of about 0.12 μM or greater, then at least a portion of the syngas being provided to the first fermentor is provided to one or more subsequent fermentors in an amount effective for providing a CO concentration in any subsequent fermentor of about 0.12 μM or less.

BRIEF DESCRIPTION OF FIGURES

The above and other aspects, features and advantages of several aspects of the process will be more apparent from the following figures.

Figure 1:
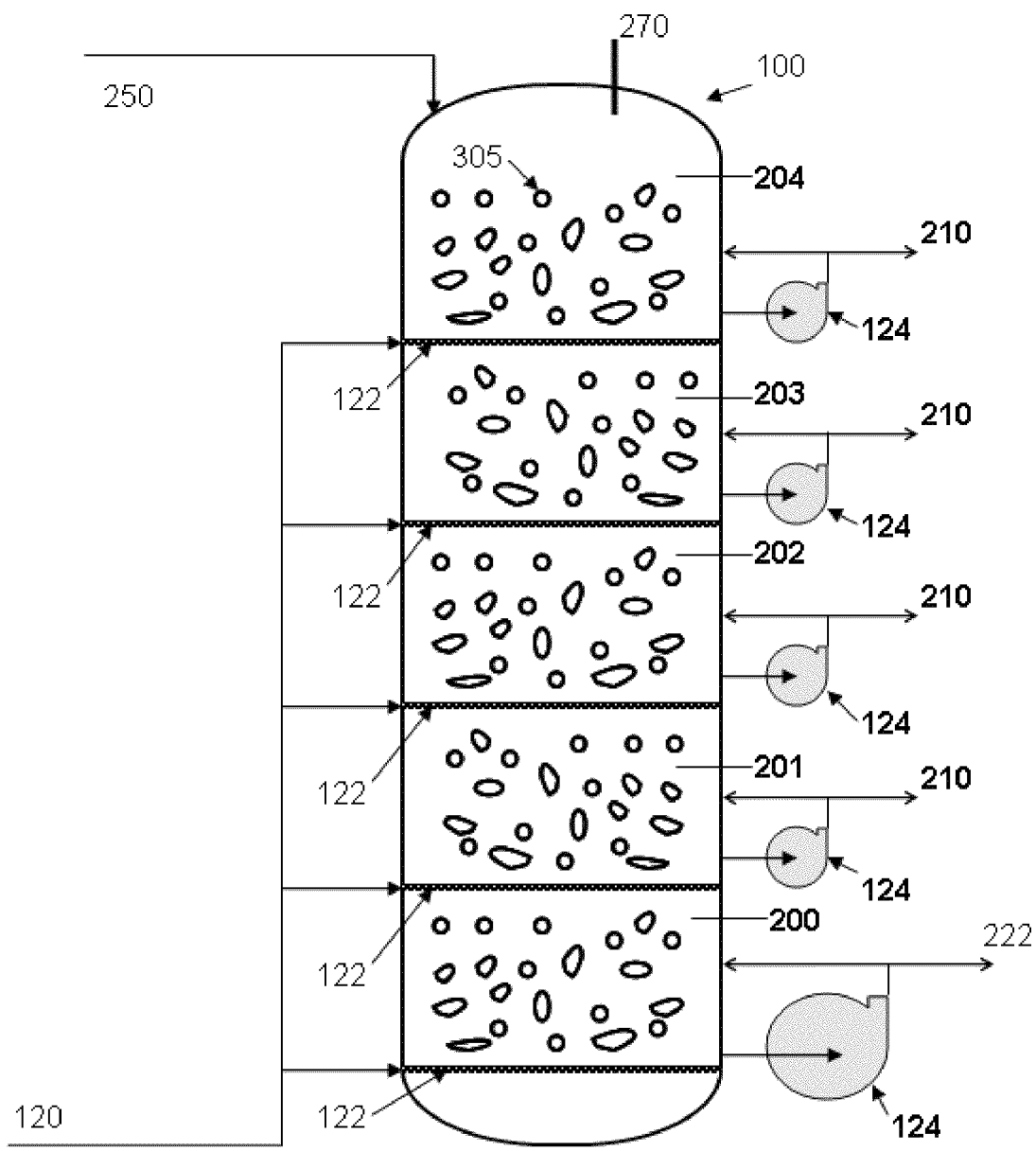
FIG. 1 is a perspective view of a fermentor with multiple fermentation zones.

Corresponding reference characters indicate corresponding components throughout the several views of the figures. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various aspects of the present process and apparatus. Also, common but well-understood elements that are useful or necessary in commercially feasible aspects are often not depicted in order to facilitate a less obstructed view of these various aspects.

DETAILED DESCRIPTION

The following description is not to be taken in a limiting sense, but is made merely for the purpose of describing the general principles of exemplary embodiments. The scope of the invention should be determined with reference to the claims.

Syngas fermentations conducted in bioreactors with medium and acetogenic bacteria as described herein are effective for providing conversions of CO in syngas into alcohols and other products. Control of CO concentrations in the fermentation through determining CO concentration in the fermentation medium is effective for providing high productivity levels. In this aspect, productivity may be expressed as STY (space time yield expressed as g ethanol/(L·day). In this aspect, the process is effective for providing a STY (space time yield) of at least about 10 g ethanol/(L·day). Possible STY values include about 10 g ethanol/(L·day) to about 200 g ethanol/(L·day), in another aspect, about 10 g ethanol/(L·day) to about 160 g ethanol/(L·day), in another aspect, about 10 g ethanol/(L·day) to about 120 g ethanol/(L·day), in another aspect, about 10 g ethanol/(L·day) to about 80 g ethanol/(L·day), in another aspect, about 20 g ethanol/(L·day) to about 140 g ethanol/(L·day), in another aspect, about 20 g ethanol/(L·day) to about 100 g ethanol/(L·day), in another aspect, about 40 g ethanol/(L·day) to about 140 g ethanol/(L·day), and in another aspect, about 40 g ethanol/(L·day) to about 100 g ethanol/(L·day).

DEFINITIONS

Unless otherwise defined, the following terms as used throughout this specification for the present disclosure are defined as follows and can include either the singular or plural forms of definitions below defined:

The term "about" modifying any amount refers to the variation in that amount encountered in real world conditions, e.g., in the lab, pilot plant, or production facility. For example, an amount of an ingredient or measurement employed in a mixture or quantity when modified by "about" includes the variation and degree of care typically employed in measuring in an experimental condition in production plant or lab. For example, the amount of a component of a product when modified by "about" includes the variation between batches in a multiple experiments in the plant or lab and the variation inherent in the analytical method. Whether or not modified by "about," the amounts include equivalents to those amounts. Any quantity stated herein and modified by "about" can also be employed in the present disclosure as the amount not modified by "about".

The term "syngas" or "synthesis gas" means synthesis gas which is the name given to a gas mixture that contains varying amounts of carbon monoxide and hydrogen. Examples of production methods include steam reforming of natural gas or hydrocarbons to produce hydrogen, the gasification of coal and in some types of waste-to-energy gasification facilities. The name comes from their use as intermediates in creating synthetic natural gas (SNG) and for producing ammonia or methanol. Syngas is combustible and is often used as a fuel source or as an intermediate for the production of other chemicals.

The term "fermentor" includes a fermentation device consisting of one or more vessels and/or towers or piping arrangements, which includes the Continuous Stirred Tank Reactor (CSTR), Immobilized Cell Reactor (ICR), Trickle Bed Reactor (TBR), Moving Bed Biofilm Reactor (MBBR), Bubble Column, Gas Lift Fermenter, Membrane Reactor such as Hollow Fibre Membrane Bioreactor (HFMBR), Static Mixer, or other vessel or other device suitable for gas-liquid contact.

The terms "fermentation", fermentation process" or "fermentation reaction" and the like are intended to encompass both the growth phase and product biosynthesis phase of the process. In one aspect, fermentation refers to conversion of CO to alcohol.

The term "cell density" means mass of microorganism cells per unit volume of fermentation broth, for example, grams/liter.

The term "increasing the efficiency", "increased efficiency" and the like, when used in relation to a fermentation process includes increasing one or more of the rate of growth of microorganisms in the fermentation, the volume or mass of desired product (such as alcohols) produced per volume or mass of substrate (such as carbon monoxide) consumed, the rate of production or level of production of the desired product, and the relative proportion of the desired product produced compared with other by-products of fermentation.

Syngas

Syngas may be provided from any know source. In one aspect, syngas may be sourced from gasification of carbonaceous materials. Gasification involves partial combustion of biomass in a restricted supply of oxygen. The resultant gas mainly includes CO and $H_2$. In this aspect, syngas will contain at least about 10 mole % CO, in one aspect, at least about 20 mole %, in one aspect, about 10 to about 100 mole %, in another aspect, about 20 to about 100 mole % CO, in another aspect, about 30 to about 90 mole % CO, in another aspect, about 40 to about 80 mole % CO, and in another aspect, about 50 to about 70 mole % CO. Some examples of suitable gasification methods and apparatus are provided in U.S. Ser. Nos. 61/516,667, 61/516,704 and 61/516,646, all of which were filed on Apr. 6, 2011, and in U.S. Ser. Nos. 13/427,144, 13/427,193 and 13/427,247, all of which were filed on Mar. 22, 2012, and all of which are incorporated herein by reference.

Depending on the syngas composition, the syngas may be provided directly to a fermentation process or may be further modified to include an appropriate $H_2$ to CO molar ratio. In one aspect, syngas provided to the fermentor has an $H_2$ to CO molar ratio of about 0.2 or more, in another aspect, about 0.25 or more, and in another aspect, about 0.5 or more. In another aspect, syngas provided to the fermentor may include about 40 mole percent or more CO plus $H_2$ and about 30 mole percent or less CO, in another aspect, about 50 mole percent or more CO plus $H_2$ and about 35 mole percent or less CO, and in another aspect, about 80 mole percent or more CO plus $H_2$ and about 20 mole percent or less CO.

In another aspect, the process has applicability to supporting the production of alcohol from gaseous substrates such as high volume CO-containing industrial flue gases. In some aspects, a gas that includes CO is derived from carbon containing waste, for example, industrial waste gases or from the gasification of other wastes. As such, the processes represent effective processes for capturing carbon that would otherwise be exhausted into the environment. Examples of industrial flue gases include gases produced during ferrous metal products manufacturing, non-ferrous products manufacturing, petroleum refining processes, gasification of coal, gasification of biomass, electric power production, carbon black production, ammonia production, methanol production and coke manufacturing.

In one aspect, a gas separator is configured to substantially separate at least one portion of the gas stream, wherein the portion includes one or more components. For example, the gas separator may separate $CO_2$ from a gas stream comprising the following components: CO, $CO_2$, $H_2$, wherein the $CO_2$ may be passed to a $CO_2$ remover and the remainder of the gas stream (comprising CO and $H_2$) may be passed to a bioreactor. Any gas separator known in the art may be utilized. In this aspect, syngas provided to the fermentor will have about 10 mole % or less $CO_2$, in another aspect, about 1 mole % or less $CO_2$, and in another aspect, about 0.1 mole % or less $CO_2$.

Certain gas streams may include a high concentration of CO and low concentrations of $H_2$. In one aspect, it may be desirable to optimize the composition of the substrate stream in order to achieve higher efficiency of alcohol production and/or overall carbon capture. For example, the concentration of $H_2$ in the substrate stream may be increased before the stream is passed to the bioreactor.

According to particular aspects of the invention, streams from two or more sources can be combined and/or blended to produce a desirable and/or optimized substrate stream. For example, a stream comprising a high concentration of CO, such as the exhaust from a steel mill converter, can be combined with a stream comprising high concentrations of $H_2$, such as the off-gas from a steel mill coke oven.

Depending on the composition of the gaseous CO-containing substrate, it may also be desirable to treat it to remove any undesired impurities, such as dust particles before introducing it to the fermentation. For example, the gaseous substrate may be filtered or scrubbed using known methods.

Bioreactor Design and Operation

In one aspect, a fermentor design may include different fermentation zones in the same fermentor. For example, a large fermentor or a bubble column type reactor may include different fermentation zones. Descriptions of fermentor designs are described in U.S. Ser. Nos. 13/471,827 and 13/471,858, both filed May 15, 2012, and U.S. Ser. No. 13/473,167, filed May 16, 2012, all of which are incorporated herein by reference.

As shown in FIG. 1, a fermentor 100 includes multiple fermentation zones 200. As shown, the fermentor 100 includes a first fermentation zone 200 and four additional fermentations zones 201, 202, 203, 204. In another aspect, the fermentor 100 may include two or more fermentation zones, and may includes from two to ten fermentation zones. A fermentation zone is defined as space above a gas inlet/sparger 122 and below the next gas/inlet sparger 122, or above a gas inlet/sparger 122 and the top of the fermentor 100. Medium, microbes and gases 305 in the fermentor 100 may flow between fermentation zones. The fermentor 100 may also include pumps 124. The pumps 124 may be used for product 222 removal and for removal of samples 210.

In one aspect, syngas enters the fermentor 100 through a syngas supply 120. The syngas supply 120 provides syngas to the gas inlet/spargers 122. Medium and nutrients may be supplied through medium/nutrient supply 250. Off-gas may exit the fermentor 100 through an off-gas port 270. Off-gas may be provided to a vent-gas boiler. The vent-gas boiler may be utilized to provide steam for energy production.

In accordance with one aspect, the fermentation process is started by addition of medium to the reactor vessel. Some examples of medium compositions are described in U.S. Ser. Nos. 61/650,098 and 61/650,093, filed May 22, 2012, and in U.S. Pat. No. 7,285,402, filed Jul. 23, 2001, all of which are incorporated herein by reference. The medium may be sterilized to remove undesirable microorganisms and the reactor is inoculated with the desired microorganisms. Sterilization may not always be required.

In one aspect, the microorganisms utilized include acetogenic bacteria. Examples of useful acetogenic bacteria include those of the genus *Clostridium*, such as strains of *Clostridium ljungdahlii*, including those described in WO 2000/68407, EP 117309, U.S. Pat. Nos. 5,173,429, 5,593,886 and 6,368,819, WO 1998/00558 and WO 2002/08438, strains of *Clostridium autoethanogenum* (DSM 10061 and DSM 19630 of DSMZ, Germany) including those described in WO 2007/117157 and WO 2009/151342 and *Clostridium ragsdalei* (P11, ATCC BAA-622) and *Alkalibaculum bacchi* (CP11, ATCC BAA-1772) including those described respectively in U.S. Pat. No. 7,704,723 and "Biofuels and Bioproducts from Biomass-Generated Synthesis Gas", Hasan Atiyeh, presented in Oklahoma EPSCoR Annual State Conference, Apr. 29, 2010 and *Clostridium carboxidivorans* (ATCC PTA-7827) described in U.S. Patent Application No. 2007/0276447. Other suitable microorganisms includes those of the genus *Moorella*, including *Moorella* sp. HUC22-1, and those of the genus *Carboxydothermus*. Each of these references is incorporated herein by reference. Mixed cultures of two or more microorganisms may be used.

Some examples of useful bacteria include *Acetogenium kivui, Acetoanaerobium noterae, Acetobacterium woodii, Alkalibaculum bacchi* CP11 (ATCC BAA-1772), *Blautia producta, Butyribacterium methylotrophicum, Caldanaerobacter subterraneous, Caldanaerobacter subterraneous pacificus, Carboxydothermus hydrogenoformans, Clostridium aceticum, Clostridium acetobutylicum, Clostridium acetobutylicum* P262 (DSM 19630 of DSMZ Germany), *Clostridium autoethanogenum* (DSM 19630 of DSMZ Germany), *Clostridium autoethanogenum* (DSM 10061 of DSMZ Germany), *Clostridium autoethanogenum* (DSM 23693 of DSMZ Germany), *Clostridium autoethanogenum* (DSM 24138 of DSMZ Germany), *Clostridium carboxidivorans* P7 (ATCC PTA-7827), *Clostridium coskatii* (ATCC PTA-10522), *Clostridium drakei, Clostridium ljungdahlii* PETC (ATCC 49587), *Clostridium ljungdahlii* ERI2 (ATCC 55380), *Clostridium ljungdahlii* C-01 (ATCC 55988), *Clostridium ljungdahlii* O-52 (ATCC 55889), *Clostridium magnum, Clostridium pasteurianum* (DSM 525 of DSMZ Germany), *Clostridium ragsdali* P11 (ATCC BAA-622), *Clostridium scatologenes, Clostridium thermoaceticum, Clostridium ultunense, Desulfotomaculum kuznetsovii, Eubacterium limosum, Geobacter sulfurreducens, Methanosarcina acetivorans, Methanosarcina barkeri, Morrella thermoacetica, Morrella thermoautotrophica, Oxobacter pfennigii, Peptostreptococcus productus, Ruminococcus productus, Thermoanaerobacter kivui*, and mixtures thereof.

Upon inoculation, an initial feed gas supply rate is established effective for supplying the initial population of microorganisms. Effluent gas is analyzed to determine the content of the effluent gas. Results of gas analysis are used to control feed gas rates. In this aspect, the process provides a CO concentration to initial cell density ratio of about 0.5 to about 0.9, in another aspect, about 0.6 to about 0.8, in another aspect, about 0.5 to about 0.7, and in another aspect, about 0.5 to about 0.6.

Upon reaching desired levels, liquid phase and cellular material is withdrawn from the reactor and replenished with medium. The process is effective for increasing cell density to about 2.0 grams/liter or more, in another aspect, about 2 to about 25 grams/liter, in another aspect, about 2 to about 20 grams/liter, in another aspect, about 2 to about 10 grams/liter, in another aspect, about 2 to about 8 grams/liter, in another aspect, about 3 to about 6 grams/liter, and in another aspect, about 4 to about 5 grams/liter.

In another aspect, the process is effective for maintaining a CO concentration ($\mu M$) to cell density (grams/liter) ratio of about 0.001 to about 1.0. In another aspect, a CO concentration to cell density ratio of about 0.01 to about 0.9, in another aspect, about 0.01 to about 0.8, in another aspect, about 0.02 to about 0.8, in another aspect, about 0.02 to about 0.75, in another aspect, about 0.03 to about 0.75, and in another aspect, about 0.03 to about 0.5.

In another aspect, the process is effective for maintaining a CO concentration ($\mu M$) to cell density (grams/liter) ratio of about 0.001 to about 1.0. In another aspect, a CO concentration to cell density ratio of about 0.01 to about 0.9, in another aspect, about 0.01 to about 0.8, in another aspect, about 0.02 to about 0.8, in another aspect, about 0.02 to about 0.75, in another aspect, about 0.03 to about 0.75, and in another aspect, about 0.03 to about 0.5.

In one aspect, syngas is supplied to a first fermentation zone 200. If a CO concentration in the first fermentation zone 200 is about 0.12 $\mu M$ or greater, then at least a portion of the syngas being supplied to the first fermentation zone 200 is provided to one or more subsequent fermentation zones through gas inlet/spargers 122. The portion of syngas provided to the one or more subsequent fermentation zones provides a CO concentration in any subsequent fermentation zone of about 0.12 $\mu M$ or less, in another aspect, about 0.10 $\mu M$ or less, in another aspect, about 0.08 $\mu M$ or less, in another aspect, about 0.06 $\mu M$ or less, in another aspect, about 0.04 $\mu M$ or less, and in another aspect, about 0.02 $\mu M$ or less.

Syngas may be supplied to each fermentation zone one at a time or may be supplied to one or more fermentation zones simultaneously. In this aspect, syngas entering a fermentation zone will have about 20 mole % or more CO, in another aspect, about 30 mole % or more, in another aspect, about 40 mole % or more, and in another aspect, about 50 mole % or more.

In another aspect, syngas supplied to any fermentation zone will have an $H_2$ to CO molar ratio of about 0.2 or more, and from about 4 mole % to about 99.9 mole % CO. In another aspect, syngas entering any subsequent fermentation zone will have an $H_2$ to CO molar ratio of about 0.5 or more, in another aspect, about 1.0 or more, and in another aspect, about 3.5 or more.

Figure 2:
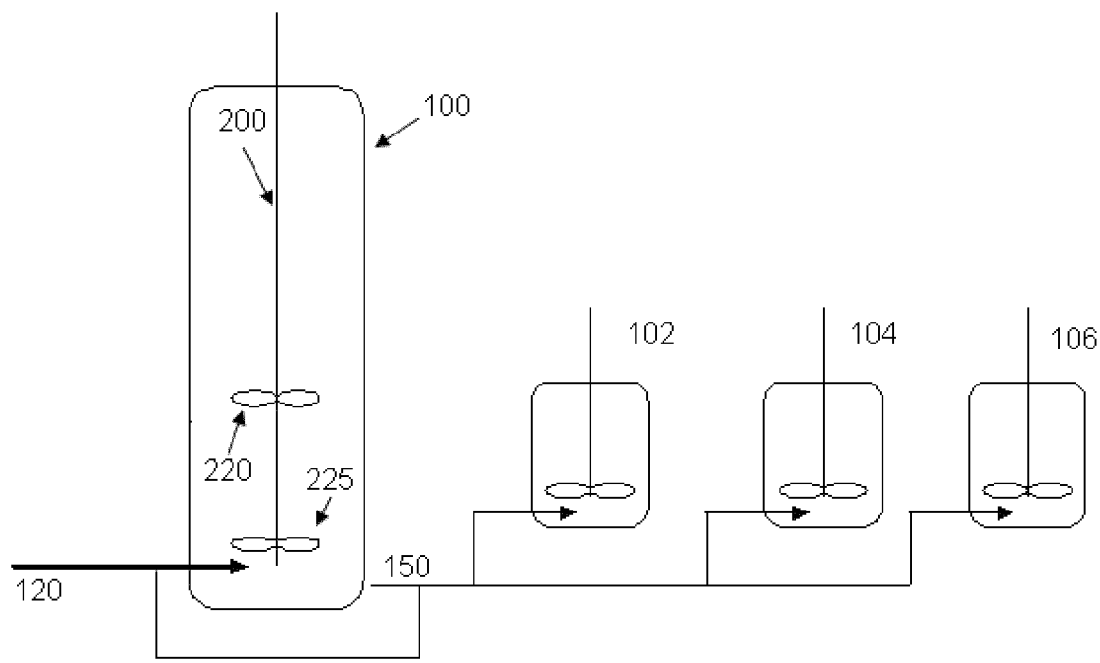
FIG. 2 is a perspective view of a series of fermentors.

Another aspect of a fermentor design is shown in FIG. 2. In this aspect, the design includes a first fermentor 100 connected in series to subsequent fermentors, such as for example, second fermentor 102, third fermentor 104, and fourth fermentor 106. The design may include any number of subsequent fermentors from 1 to about 10 (for example, 1, 2, 3, 4, 5, 6, 7, 8, 9 or 10 subsequent fermentors).

In one aspect, syngas enters the first fermentor 100 through a gas inlet/sparger 120. Dispersion of the syngas and further mixing is accomplished with at least one gas dispersion impeller 225 and at least one mixing impeller 220 which are coupled to a drive shaft 200.

Syngas 150 may be conveyed to one or more subsequent bioreactors. Syngas 150 may be supplied to each subsequent fermentor one at a time in series, or may be supplied to one or more subsequent fermentors simultaneously in parallel. In this aspect, the syngas entering any subsequent fermentor will have about 20 mole % or more CO, in another aspect, about 30 mole % or more, in another aspect, about 40 mole % or more, and in another aspect, about 50 mole % or more.

In another aspect, syngas supplied to any subsequent fermentor will have an $H_2$ to CO molar ratio of about 0.2 or more, and from about 4 mole % to about 99.9 mole % CO. In another aspect, syngas entering any subsequent fermentor will have an $H_2$ to CO molar ratio of about 0.5 or more, in another aspect, about 1.0 or more, and in another aspect, about 3.5 or more.

In another aspect, off-gas from a first or any subsequent fermentor may be provided to a vent-gas boiler. The vent-gas boiler may be utilized to provide steam for energy production.

Alcohol Productivity

Certain ratios of $H_2$ to CO and/or $CO_2$ to CO are effective for providing enhanced STY. In this aspect, the process is effective for providing a STY (space time yield) of about 1 gram or more total alcohol/(L·day). In another aspect, the process is effective for providing a providing a STY of at least about 10 g total alcohol/(L·day). Possible STY values include about 10 g total alcohol/(L·day) to about 300 g/(L·day), in another aspect, about 10 g total alcohol/(L·day) to about 200 g total alcohol/(L·day), in another aspect, about 10 g total alcohol/(L·day) to about 160 g total alcohol/(L·day), in another aspect, about 10 g total alcohol/(L·day) to about 120 g total alcohol/(L·day), in another aspect, about 10 g total alcohol/(L·day) to about 80 g total alcohol/(L·day), in another aspect, about 20 g total alcohol/(L·day) to about 140 g total alcohol/(L·day), in another aspect, about 20 g total alcohol/(L·day) to about 100 g total alcohol/(L·day), in another aspect, about 40 g total alcohol/(L·day) to about 140 g total alcohol/(L·day), and in another aspect, about 40 g total alcohol/(L·day) to about 100 g total alcohol/(L·day).

As used herein, "total alcohol" includes ethanol, butanol, propanol and methanol. In one aspect, the total alcohol may include at least about 80 weight percent or more ethanol. In another aspect, total alcohol may include at least about 25 weight percent or less butanol.

In a related aspect, productivity may be expressed as STY (space time yield expressed as g ethanol/(L·day)). In this aspect, the process is effective for providing a STY (space time yield) of at least about 10 g ethanol/(L·day). Possible STY values include about 10 g ethanol/(L·day) to about 200 g ethanol/(L·day), in another aspect, about 10 g ethanol/(L·day) to about 160 g ethanol/(L·day), in another aspect, about 10 g ethanol/(L·day) to about 120 g ethanol/(L·day), in another aspect, about 10 g ethanol/(L·day) to about 80 g ethanol/(L·day), in another aspect, about 20 g ethanol/(L·day) to about 140 g ethanol/(L·day), in another aspect, about 20 g ethanol/(L·day) to about 100 g ethanol/(L·day), in another aspect, about 40 g ethanol/(L·day) to about 140 g ethanol/(L·day), and in another aspect, about 40 g ethanol/(L·day) to about 100 g ethanol/(L·day).

Determination of CO Concentrations—Direct Measurement

Sampling:

In one aspect, the process includes contacting an aliquot of fermentation medium with at least one CO binding ligand and at least one microbial activator. The process may include taking an aliquot of fermentation medium directly from the bioreactor or from various recycle loops associated with the bioreactor. The amount of fermentation medium removed corresponds to any amount effective for providing an accurate determination of CO concentration. In this aspect, the amount of fermentation medium removed is adjusted based on expected CO concentration levels. Generally, sample amounts will range from about 0.02 ml to about 20 ml, in another aspect, 1 ml to about 7 ml, in another aspect, about 0.1 ml to about 1 ml, in another aspect about 5 ml to about 10 ml, and in another aspect about 7 ml to about 8 ml.

Aliquots removed from the bioreactor will include fermentation medium and microbes capable of producing and/or consuming CO. Fermentation mediums may include known mediums as described herein. Microbes capable of producing and/or consuming CO include acetogenic bacteria as described herein. In one aspect, the process may include removal of microbes from the aliquots of fermentation medium prior to CO measurements. In another aspect, the process may include analysis without removal of microbes.

In one aspect, sampling may be conducted using any type of sampling probe known in the art. One example of an appropriate sampling probe is an FISP® probe (available from Flownamics). The FISP® probe is a sampling probe capable of withdrawing sterile, cell-free samples from the fermentor. FISP® allows direct on-line sample transfer to a variety of analyzers, such as biochemistry and HPLC systems, as well as collection for off-line analysis. FISP® is a small, tube-shaped, sterilizable 316 stainless steel carrier which is surrounded by a tubular, micro-porous membrane.

In another aspect, tubing utilized for sampling should be gas impermeable. In this aspect, tubing should be non-metallic and non-ferrous. On example of tubing that may be utilized includes tubing made from polyetheretherketone.

CO Binding Ligand:

CO binding ligands are effective for bonding to dissolved CO in the fermentation medium. In another aspect, examples of CO binding ligands include hemoglobin, myoglobin, free heme, heme containing compounds, and mixtures thereof.

In an alternative aspect, the CO binding ligand includes a chelating agent. In this aspect, the chelating agent is a non-heme containing compound capable of binding CO.

Amounts of CO binding ligand utilized will be in an excess of the amount of CO that may be in the sample. Generally, the amount of CO binding ligand utilized in the process will be about 7 mg/ml or more.

Microbial Inactivator:

Microbial inactivators are effective for preventing any microbes in the sample from consuming or creating CO. In this aspect, microbial inactivators may include salt, acid, base, oxidizing agents, organic solvent, heat, cold, and mixtures thereof. In the aspect where the microbial inactivator is a salt, the salt may include NaCl, KCl, ammonium chloride, sodium sulfate, sodium bromide, and mixtures thereof. The salt solution will be at a concentration effective for inactivating microbes capable of consuming or creating CO. In this aspect, the salt solution will have a concentration of 0.2 to about 5 M.

In the aspect where the microbial inactivator is an acid or base, the acid may include HCl, sulfuric acid, trifluroacetic acid, acetic acid, and mixtures thereof, and the base may include NaOH, ammonium hydroxide, triethylamine, potassium hydroxide, and mixtures thereof. The acid or base solution will be at a concentration effective for inactivating microbes capable of consuming or creating CO. In this aspect, the acid solution will have a concentration of about 0.02 to about 5 M, and the base will have a concentration of about 0.02 to about 5 M. In this aspect, where the inactivator is hydrogen peroxide, the concentration may be from about 1% to about 3%. In the aspect where cold is used, temperatures from about $-270°$ C. to about $0°$ C. are effective. In the aspect where heat is used, temperatures from about $35°$ C. to about $100°$ C. are effective.

Absorbance Measurement:

Any known spectrophotometric equipment may provide absorbance measurements. Some examples of spectrophotometric equipment include Beckman Coulter sectrophotometers (DU 800, DU730) and microplate readers such as the Spectramax (M1, M2, and M3). In this aspect, a ratio of absorbance measurements at 538 nm and 555 nm provides a measure of CO bound to CO binding ligand. In another aspect, the process may include use of a flow through cell in connection with an appropriate spectrophotometer to provide continuous absorbance measurements.

In one aspect, if direct measurement of CO indicates a CO concentration in the fermentation medium of about 0.12 µM or more, then at least a portion of the syngas provided to the first fermentor is provided a one or more subsequent fermentors either operating in series or in parallel. The amount of syngas provided to the one of more subsequent fermentors is effective for providing a CO concentration in the fermentation medium of any subsequent fermentor of about 0.12 µM or less (as determined by direct measurement).

EXAMPLES

Example 1

Measurement of CO

Hemoglobin Solution was Prepared as Follows:

A 7 mg/ml solution of bovine hemoglobin was prepared in a 100 mM carbonate buffer (pH 9.3). Sodium dithionite (20 mg/ml) was added and the mixture was centrifuged at 7500 g at $4°$ C. Supernatant was removed and one half volume of 5M NaCl was added.

Standards were Prepared as Follows:

A syngas sparged water solution (0.0, 0.01, 0.02, 0.05, 0.1, 0.2 and 0.3 ml) was added to a 0.6 ml of hemoglobin/salt solution in a 2 ml centrifuge tube. Water was added to bring total volumes to 2.0 ml.

Sampling was Conducted as Follows:

Hemoglobin/salt solution was drawn into a serological syringe equipped with a stopcock. Sampling of fermentate was conducted by drawing a sample from a cell recycle system from a "T" off a main line from a bioreactor that was fermenting syngas. Lines were first cleared by withdrawing about 10 ml of fermentate. A 7 ml aliquot of fermentate was then rapidly removed with the syringe containing the hemoglobin/salt solution pointing downward to effect mixing the fermentate with the hemoglobin/salt solution.

Absorbance Measurements were Conducted as Follows:

All samples and standards were held at room temperature for a minimum of 10 minutes and a maximum of 2 hours. Absorbance of standards and samples was determined at 538 nm and 555 nm.

Calculating CO Concentration:

Using a Henry's Law constant of 0.00095 M/atm, stock concentrations of CO were calculated based on a percentage of CO in the syngas. A standard curve showing a ratio of absorbance at 538:555 nm versus CO concentration in µM was prepared.

While the invention herein disclosed has been described by means of specific embodiments, examples and applications thereof, numerous modifications and variations could be made thereto by those skilled in the art without departing from the scope of the invention set forth in the claims.

What is claimed is:

1. A method for reducing growth inhibition by carbon monoxide (CO) of microbes in fermentation, comprising:
   a) providing syngas to a first fermentation zone;
   b) fermenting the syngas; and
   c) determining the CO concentration in the fermentation medium in the first fermentation zone, wherein if the CO concentration in the fermentation medium in the first fermentation zone has a calculated value of 0.12 µM or greater, then at least a portion of the syngas being provided to the first fermentation zone is provided to one or more subsequent fermentation zones in an amount effective for providing a CO concentration in the first fermentation zone of at least 0.12 µM or less.

2. The process of claim 1 wherein the CO concentration is determined by contacting an aliquot of fermentation medium with at least one CO binding ligand and at least one microbial inactivator, and measuring the amount of CO bound to the CO binding ligand.

3. The process of claim 2 wherein the CO bonding ligand is selected from the group consisting of hemoglobin, myoglobin, free heme, heme containing compounds and mixtures thereof.

4. The process of claim 2 wherein the microbial inactivator is selected from the group consisting of salt, acid, base, organic solvent, oxidizing agents, heat, cold, and mixtures thereof.

5. The process of claim 2 wherein the amount of CO bound to the CO binding ligand is measured by determining changes in absorbance.

6. The process of claim 1 wherein the syngas provided to the first or any one or more subsequent fermentation zones has a molar ratio of $H_2$ to CO of 0.2 or more.

7. The process of claim 1 wherein the syngas provided to the first or any one or more subsequent fermentation zones has 40 mole percent or more of CO plus $H_2$ and an $H_2$ content of 30 mole percent or less.

8. The process of claim 1 wherein the syngas provided to the first or any one or more subsequent fermentation zones has a $CO/CO_2$ molar ratio of at least 0.75.

9. The process of claim 1 wherein the process is effective for increasing cell density to 2.0 g/L or more in the first or any one or more subsequent fermentation zones.

10. The process of claim 1 wherein the process provides a CO concentration to initial cell density ratio of 0.5 to 0.9.

11. The process of claim 1 wherein the process is effective for maintaining a CO concentration to cell density ratio of 0.001 to 1.0.

12. The process of claim 1 wherein the fermentation medium includes microbes capable of consuming and/or producing CO.

13. The process of claim 12 wherein the microbes are acetogenic bacteria.

14. The process of claim 13 wherein the acetogenic bacteria are selected from the group consisting of *Acetogenium kivui, Acetoanaerobium noterae, Acetobacterium woodii, Alkalibaculum bacchi* CP11 (ATCC BAA-1772), *Blautia producta, Butyribacterium methytotrophicum, Caldanaerobacter subterraneous, Caldanaerobacter subterraneous pacificus, Carboxydothermus hydrogenoformans, Clostridium aceticum, Clostridium acetobutylieum, Clostridium acetobutylicum* P262, *Clostridium autoethanogenum, Clostridium autoethanogenum* (DSM 10061 of DSMZ Germany), *Clostridium autoethanogenum* (DSM 23693 of DSMZ Germany), *Clostridium autoethanogenum* (DSM 24138 of DSMZ Germany), *Ctostridium carboxidivorans* P7 (ATCC PTA-7827), *Clostridium coskatii* (ATCC PTA-10522), *Ctostridium drakei, Clostridium ljungdahlii* PETC (ATCC 49587), *Clostridium ljungdahlii* ERI2 (ATCC 55380), *Clostridium ljungdahlii* C-01 (ATCC 55988), *Clostridium ljungdahlii* O-52 (ATCC 55889), *Clostridium magnum, Clostridium pasteurianum* (DSM 525 of DSMZ Germany), *Clostridium ragsdali* P11 (ATCC BAA-622), *Clostridium scatologenes, Ctostridium thermoaceticum, Clostridium ultunense, Desulfotomaculum kuznetsovii, Eubacterium limosum, Geobacter sulfurreducens, Methanosarcina acetivorans, Methanosarcina barkeri, Morrella thermoaeetica, Morrella thermoautotrophica, Oxobacter pfennigii, Peptostreptococcus productus, Ruminococcus productus, Thermoanaerobacter kivui* and mixtures thereof.

15. A method for reducing growth inhibition by carbon monoxide (CO) of microbes in fermentation, comprising:
   a) providing syngas to a first fermentor;
   b) fermenting the syngas; and
   c) determining the CO concentration in the fermentation medium in the first fermentor, wherein if the CO concentration in the fermentation medium in the first fermentor has a calculated value of 0.12 μM or greater, then at least a portion of the syngas being provided to the first fermentor is provided to one or more subsequent fermentors in an amount effective for providing a CO concentration in the first fermentor of at least 0.12 μM or less.

16. The process of claim 1 wherein the CO concentration is determined by contacting an aliquot of fermentation medium with at least one CO binding ligand and at least one microbial inactivator, and measuring the amount of CO bound to the CO binding ligand.

17. The process of claim 16 wherein the CO bonding ligand is selected from the group consisting of hemoglobin, myoglobin, free heme, heme containing compounds and mixtures thereof.

18. The process of claim 16 wherein the microbial inactivator is selected from the group consisting of salt, acid, base, organic solvent, oxidizing agents, heat, cold, and mixtures thereof.

19. The process of claim 16 wherein the amount of CO bound to the CO binding ligand is measured by determining changes in absorbance.

20. The process of claim 15 wherein the syngas provided to the first or any one or more subsequent fermentors has a molar ratio of $H_2$ to CO of 0.2 or more.

21. The process of claim 15 wherein the syngas provided to the first or any one or more subsequent fermentors has 40 mole percent or more of CO plus $H_2$ and an $H_2$ content of 30 mole percent or less.

22. The process of claim 15 wherein the syngas provided to the first or any one or more subsequent fermentors has a $CO/CO_2$ molar ratio of at least 0.75.

23. The process of claim 15 wherein the process is effective for increasing cell density to 2.0 g/L or more in the first or any one or more subsequent fermentors.

24. The process of claim 15 wherein the process provides a CO concentration to initial cell density ratio of 0.5 to 0.9.

25. The process of claim 15 wherein the process is effective for maintaining a CO concentration to cell density ratio of 0.001 to 1.0.

26. The process of claim 15 wherein the fermentation medium includes microbes capable of consuming and/or producing CO.

27. The process of claim 26 wherein the microbes are acetogenic bacteria.

28. The process of claim 27 wherein the acetogenic bacteria are selected from the group consisting of *Acetogenium kivui, Acetoanaerobium noterae, Acetobacterium woodii, Alkalibaculum bacchi* CP11 (ATCC BAA-1772), *Blautia producta, Butyribacterium methytotrophicum, Caldanaerobacter subterraneous, Caldanaerobacter subterraneous pacificus, Carboxydothermus hydrogenoformans, Clostridium aceticum, Clostridium acetobutylieum, Clostridium acetobutylicum* P262, *Clostridium autoethanogenum, Clostridium autoethanogenum* (DSM 10061 of DSMZ Germany), *Clostridium autoethanogenum* (DSM 23693 of DSMZ Germany), *Clostridium autoethanogenum* (DSM 24138 of DSMZ Germany), *Ctostridium carboxidivorans* P7 (ATCC PTA-7827), *Clostridium coskatii* (ATCC PTA-10522), *Ctostridium drakei, Clostridium ljungdahlii* PETC (ATCC 49587), *Clostridium ljungdahlii* ERI2 (ATCC 55380), *Clostridium ljungdahlii* C-01 (ATCC 55988), *Clostridium ljungdahlii* O-52 (ATCC 55889), *Clostridium magnum, Clostridium pasteurianum* (DSM 525 of DSMZ Germany), *Clostridium ragsdali* P11 (ATCC BAA-622), *Clostridium scatologenes, Ctostridium thermoaceticum, Clostridium ultunense, Desulfotomaculum kuznetsovii, Eubacterium limosum, Geobacter sulfurreducens, Methanosarcina acetivorans, Methanosarcina barkeri, Morrella thermoaeetica, Morrella thermoautotrophica, Oxobacter pfennigii, Peptostreptococcus productus, Ruminococcus productus, Thermoanaerobacter kivui* and mixtures thereof.

29. The process of claim 15 wherein syngas is provided to one or more subsequent fermentors operating in parallel.

30. The process of claim 15 wherein syngas is provided to one or more subsequent fermentors operating in series.

31. The process of claim 15 wherein the first or one or more subsequent fermentors are different fermentation zones in the fermentor.

32. The process of claim 15 wherein at least a portion of the off-gas from a first or any one or more subsequent fermentors is provided to a vent-gas boiler.

* * * * *